US010857339B2

(12) United States Patent
Richardson et al.

(10) Patent No.: US 10,857,339 B2
(45) Date of Patent: Dec. 8, 2020

(54) IMPLANTABLE ACCESS PORT INCLUDING FLUID HANDLING FEATURES

(71) Applicant: C. R. Bard, Inc., Murray Hill, NJ (US)

(72) Inventors: Elizabeth Richardson, Clinton, MD (US); Jeremy B. Cox, Salt Lake City, UT (US); Jason R. Stats, Layton, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 21 days.

(21) Appl. No.: 16/192,430

(22) Filed: Nov. 15, 2018

(65) Prior Publication Data

US 2019/0083771 A1 Mar. 21, 2019

Related U.S. Application Data

(62) Division of application No. 14/308,962, filed on Jun. 19, 2014, now Pat. No. 10,130,803.

(Continued)

(51) Int. Cl.
*A61M 39/02* (2006.01)
*A61M 39/04* (2006.01)

(52) U.S. Cl.
CPC ........ *A61M 39/0208* (2013.01); *A61M 39/04* (2013.01); *A61M 2039/0226* (2013.01)

(58) Field of Classification Search
CPC ........... A61M 39/0208; A61M 39/0211–0244; A61M 39/04
See application file for complete search history.

(56) References Cited

U.S. PATENT DOCUMENTS 4,760,837 A 8/1988 Petit
4,772,263 A * 9/1988 Dorman ............ A61M 5/14276 128/DIG. 12

(Continued)

FOREIGN PATENT DOCUMENTS

WO 2014205197 12/2014

OTHER PUBLICATIONS

PCT/US14/43148 filed Jun. 19, 2014 International Search Report and Written Opinion dated Dec. 22, 2014.

(Continued)

*Primary Examiner* — Bhisma Mehta
*Assistant Examiner* — James D Ponton
(74) *Attorney, Agent, or Firm* — Rutan & Tucker LLP

(57) ABSTRACT

An access port for subcutaneous implantation is typically connected to a catheter, a distal portion of which is disposed within a vein or other vessel of the patient. The access port described herein is configured with enhanced fluid handling features to improve fluid flow therethrough while reducing the likelihood of clotting or occlusions in the attached catheter, thus improving system patency. The access port includes a body defining a reservoir, a needle-penetrable septum covering the top opening of the reservoir, a stem including a lumen in fluid communication with the reservoir, and a volume control device positioned in the reservoir. The volume control device includes a floor designed to move from a first position below the side opening to a second position adjacent the bottom surface, and a spring element positioned between the floor and the bottom surface, the spring element biasing the floor in the first position.

14 Claims, 6 Drawing Sheets

Related U.S. Application Data

(60) Provisional application No. 61/837,061, filed on Jun. 19, 2013.

(56) References Cited

U.S. PATENT DOCUMENTS

| | | | | |
|---|---|---|---|---|
| 4,832,054 | A | 5/1989 | Bark | |
| 5,006,115 | A * | 4/1991 | McDonald ........ | A61M 39/0208 604/175 |
| 5,833,654 | A | 11/1998 | Powers et al. | |
| 6,478,783 | B1 * | 11/2002 | Moorehead ....... | A61M 5/14276 604/132 |
| 6,537,505 | B1 | 3/2003 | LaBudde et al. | |
| 2006/0264898 | A1 | 11/2006 | Beasley et al. | |
| 2008/0027398 | A1 | 1/2008 | McKinnon et al. | |
| 2010/0298806 | A1 | 11/2010 | Yandell | |
| 2012/0109068 | A1 | 5/2012 | Vendely | |
| 2014/0378942 | A1 | 12/2014 | Christian et al. | |

OTHER PUBLICATIONS

U.S. Appl. No. 14/308,962, filed Jun. 19, 2014 Advisory Action dated Aug. 3, 2017.

U.S. Appl. No. 14/308,962, filed Jun. 19, 2014 Advisory Action dated May 8, 2018.

U.S. Appl. No. 14/308,962, filed Jun. 19, 2014 Final Office Action dated Apr. 19, 2017.

U.S. Appl. No. 14/308,962, filed Jun. 19, 2014 Non-Final Office Action dated Dec. 1, 2016.

U.S. Appl. No. 14/308,962, filed Jun. 19, 2014 Non-Final Office Action dated Oct. 2, 2017.

U.S. Appl. No. 14/308,962, filed Jun. 19, 2014 Notice of Allowance dated Jul. 13, 2018.

U.S. Appl. No. 14/308,962, filed Jun. 19, 2014 Non-Final Office Action dated Jun. 3, 2016.

* cited by examiner

IMPLANTABLE ACCESS PORT INCLUDING FLUID HANDLING FEATURES

CROSS-REFERENCE TO RELATED APPLICATIONS

This application is a division of U.S. patent application Ser. No. 14/308,962, filed Jun. 19, 2014, now U.S. Pat. No. 10,130,803, which claims the benefit of U.S. Provisional Patent Application No. 61/837,061, filed Jun. 19, 2013, and titled "Implantable Access Port Including Fluid Handling Features," each of which is incorporated herein by reference in its entirety.

BRIEF SUMMARY

Briefly summarized, embodiments of the present invention are directed to an access port for subcutaneous implantation into a body of a patient. The port is typically subcutaneously connected to a catheter, a distal portion of which is disposed within a vein or other vessel of the patient. Percutaneous access to the port via a needle can enable a clinician to infuse medicaments through the port and catheter into the vessel of the patient. The port is configured with enhanced fluid handling features to improve fluid flow therethrough while reducing the likelihood of clotting or occlusions in the attached catheter, thus improving system patency.

In one embodiment, for instance, an implantable access port is disclosed and comprises a body defining a reservoir, a needle-penetrable septum covering an opening to the reservoir, a stem defining an outlet to the reservoir, and a deformable element included in the reservoir. The deformable element is operably connected to a main portion of the septum and deforms in response to displacement of the septum so as to counteract a change in volume within the reservoir and prevent blood ingress into the catheter, where it could otherwise clot and occlude the catheter. Other fluid handling aspects of an access port are also disclosed.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to an access port for subcutaneous implantation into a body of a patient. The port is typically subcutaneously connected to a catheter, a distal portion of which is disposed within a vein or other vessel of the patient. Percutaneous access to the port via a needle can enable a clinician to infuse medicaments through the port and catheter into the vessel of the patient. Likewise, fluids can be aspirated from the vessel, via the catheter, port, and needle.

In accordance with one embodiment, the port is configured with enhanced fluid handling features to improve fluid flow therethrough while reducing the likelihood of clotting or occlusions in the attached catheter, thus improving system patency. Further details regarding these enhancements are given below.

Figure 1:
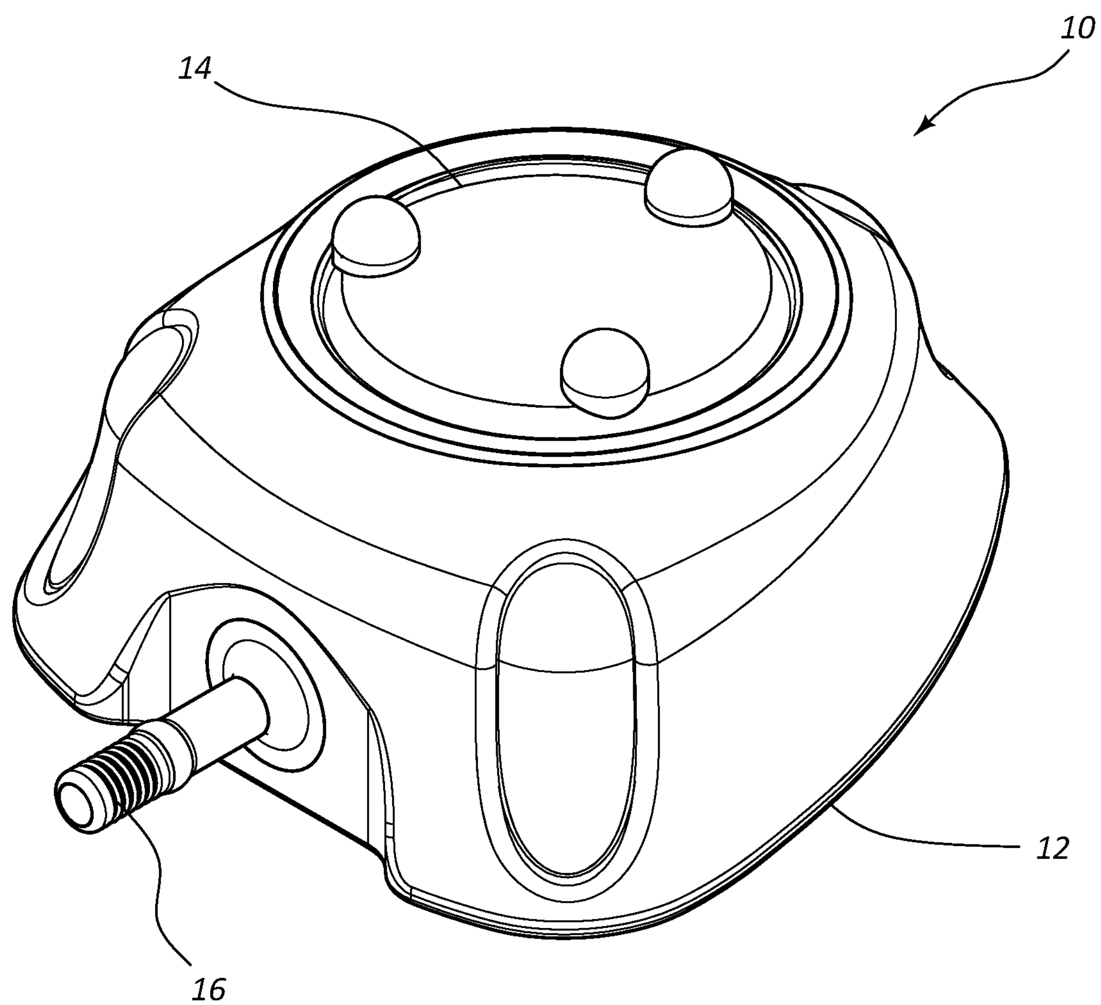
FIG. 1 is a perspective view of an implantable access port according to one embodiment.
Figure 2A:
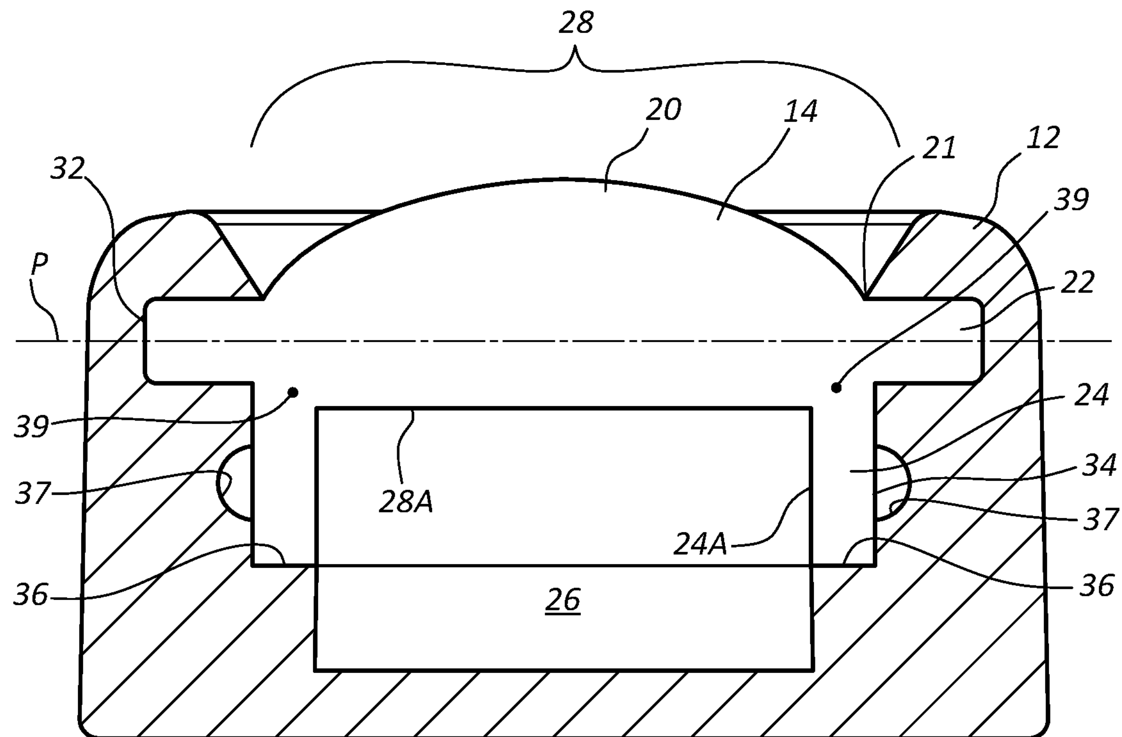
FIGS. 2A and 2B are simplified cross-sectional views of an access port according to one embodiment.

Reference is first made to FIG. 1, which depicts an implantable access port ("port"), generally designated at 10, configured in accordance with one embodiment. As shown, the port 10 includes a body 12 that defines a reservoir (FIG. 2A). A compliant, needle-penetrable septum 14 covers the reservoir and provides needle access thereto. A stem 16 extends from the port body 12 and is configured to operably connect to a proximal end of a catheter that is in turn disposed in the vasculature of a patient. In this way, vascular access to the patient by a clinician is provided via the catheter, connected access port, and skin-penetrating needle, such as an infusion set needle, for instance.

Figure 2B:
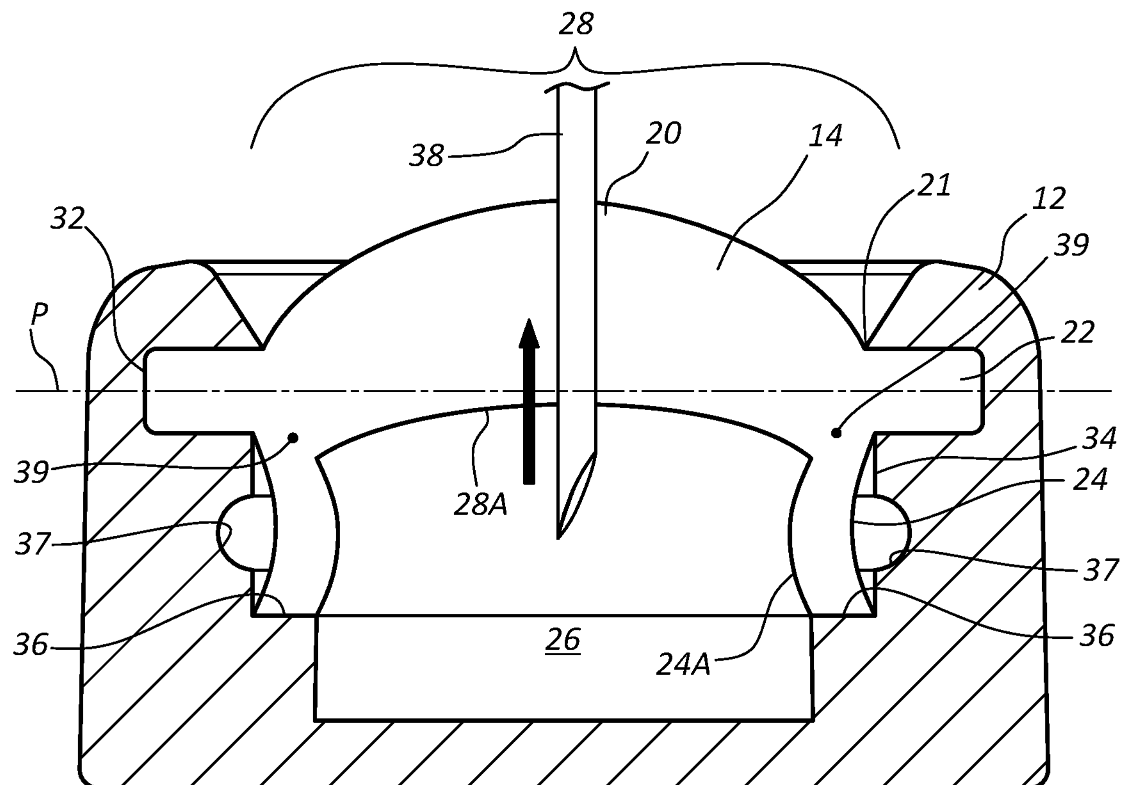

FIGS. 2A and 2B show a simplified, cross sectional view of an access port similar to the port 10 of FIG. 1. In particular, FIGS. 2A and 2B show the reservoir 26 that is defined by the port body 12, and the manner in which the septum 14 is disposed in a reservoir opening, or aperture 21, which is defined by the port body such that the septum covers and isolates the reservoir 26.

In further detail, the septum 14 includes a body 20 and an annular flange 22 that radially extends from a main portion, or central portion, 28 of the septum. Note that the main portion as used herein includes any portion of the septum through which a needle can penetrate during use of the port, though the size and extent of the main portion of the septum can vary in other embodiments. The septum flange 22 is received into an annular groove 32 defined by the port body 12. The groove 32 is disposed proximate the aperture 21 in the present embodiment, and the fit between the flange 22 and the groove is such that the septum 14 is secured in place so as to sealably enclose the reservoir 26. As shown in FIGS. 2A and 2B, then, the central portion 28 and flange 22 of the septum body 20 extend along a horizontal plane P.

In accordance with the present embodiment, FIGS. 2A and 2B show that the septum 14 further includes a deformable element, such as a skirt, or cylindrical extension 24, which extends substantially perpendicularly from the plane P of the central portion 28 of the septum body 20. As shown from the perspective of FIGS. 2A and 2B, the cylindrical extension 24 extends circumferentially downward from proximate a junction of the central portion 28 and the flange 22 of the septum body 20. As such, a central axis of the cylindrical extension 24 extends perpendicularly with respect to the plane P. Note that the location of the cylindrical extension, as well as its geometric shape, size, thickness, etc., can vary from what is shown and described herein.

FIG. 2A further shows that the cylindrical extension 24 of the septum 14 is seated within a correspondingly-sized cylindrical recess 34 that is circumferentially defined about the periphery of the reservoir 26. An annular bottom portion of the cylindrical extension 24 is affixed to a circumferential attachment surface, which in the present embodiment is defined by a shoulder 36 at the bottom of the cylindrical recess 34. Such attachment between the shoulder 36 and the bottom portion of the cylindrical extension 24 can be achieved via mechanical affixation, adhesive, or other suitable method.

FIG. 2B shows further details regarding operation of the septum 14, and the cylindrical extension 24 as a deformable element, during use of the port 10. A hollow needle 38 (such as found in an infusion set) or other suitable cannula is typically inserted through the septum central portion 28 such that a distal tip thereof is disposed within the reservoir 26. In this position, the needle 38 can infuse fluids into the port reservoir 26, which fluids then exit the reservoir via the port stem 16 (FIG. 1) and pass through the attached catheter and into the vein or other portion of the patient's vasculature. Once infusion is complete, the needle 38 is removed from the septum central portion 28 by exerting an upward pulling force thereon. Because the septum 14 is made from a compliant compressible material, such as silicone in one embodiment, pulling of the needle from the septum 14 causes the central portion 28 of the septum to deform, or be displaced, in a vertically upward direction due to compressive friction between the needle and the septum. An example amount of deformation caused by such needle removal can be seen by the upward deformation of a bottom surface 28A of the central portion 28 of the septum in FIG. 2B as the needle 38 is withdrawn upward.

Without some form of compensation, the above-described deformation of the central portion 28 of the septum 14 as shown in FIG. 2B causes a temporary increase in volume of the reservoir 26. If left unchecked, the increase in reservoir volume can in turn produce a vacuum force within the reservoir. Production of the vacuum force within the reservoir can cause blood from the vein to be aspirated a short distance into the distal end of the catheter lumen, where it can clot, thus undesirably occluding the catheter.

In accordance with one embodiment, the cylindrical extension 24 of the septum 14 is configured to compensate for the above effects caused by removal of the needle 38 from the septum. In particular, the cylindrical extension 24 of the septum 14 serves in the present embodiment as a compensation portion to compensate for and negate the increase in reservoir volume and the consequent production of vacuum force within the reservoir 26. It is noted that the cylindrical extension 24 operates, as described below, about a pivot 39 that is established by the securement of: 1) the flange 22 of the septum body 20 in the port body groove 32; and 2) the bottom portion of the cylindrical extension 24 to the shoulder 36. So configured, the pivot 39 is a loop defined annularly about an upper portion of the cylindrical extension 24, though it is appreciated that the particular shape and location of the pivot 39 can vary according to desired cylindrical extension flexing, size and configuration of the septum, etc.

The above-described securement of the cylindrical extension 24 and the corresponding pivot 39 enables the cylindrical extension—which as described in the present embodiment includes compliant silicone and is integrally formed with the septum central portion 28—to compliantly and laterally move, i.e., bulge, or flex, radially inward toward the center of the reservoir 26 in response to the upward deformation of the septum central portion 28 described above. The degree of flexing of the cylindrical extension 24 in one embodiment is shown in FIG. 2B, wherein an inner surface 24A of the cylindrical extension bulges radially inward. The inward flexing of the cylindrical extension 24 of the septum 14 reduces the volume of the reservoir 26, thus compensating for the increased reservoir volume caused by the septum central portion displacement. The net result is that the volume of the reservoir 26 remains substantially constant during needle withdrawal from the septum 14, and no vacuum force is created therein. Thus, no aspiration of blood into the distal tip of the catheter occurs, and the catheter lumen remains patent.

Note that the reservoir in the illustrated embodiment defines an annular cavity 37 about the interior side surface of the reservoir adjacent to the cylindrical extension so as to encourage separation of the cylindrical extension from a side surface of the reservoir. Though shown in cross section here as semi-circular, the annular cavity 37 can define other shapes, including square, triangular, etc., and can be positioned in different locations within the reservoir and include different sizes, etc. In yet another embodiment, no annular cavity is included within the reservoir.

Once the needle has been fully retracted from the central portion 28 of the septum 14, the central portion resiliently returns to its original shape, as shown in FIG. 2A, thus causing the cylindrical extension 24 of the septum to pivot back to its original, un-flexed configuration, also shown in FIG. 2A.

Note that, though they are integrally formed here, in one embodiment the cylindrical extension and septum are separate components but operably mated such that deformation of the central portion of the septum causes the cylindrical extension to correspondingly flex or move to compensate for the change in reservoir volume. Also, in one embodiment the cylindrical extension can include two or more pieces that do not fully encircle reservoir but nonetheless flex inward a sufficient amount to compensate for the deformation of the septum central portion. In addition, the septum can be formed of other resilient materials in addition to silicone. Note that, in one embodiment, the amount of cylindrical extension deformation is proportional to the amount of septum central portion displacement, given the pivoting action described herein.

Figure 3A:
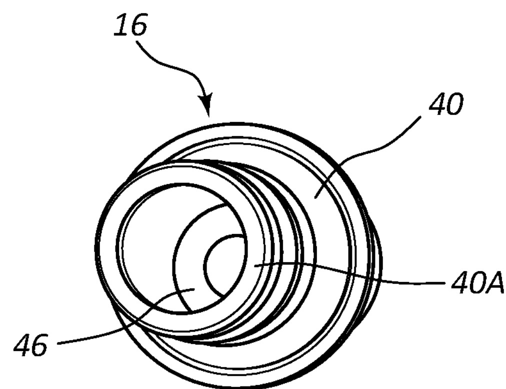
FIGS. 3A and 3B are various views of a stem of an access port according to one embodiment.
Figure 3B:
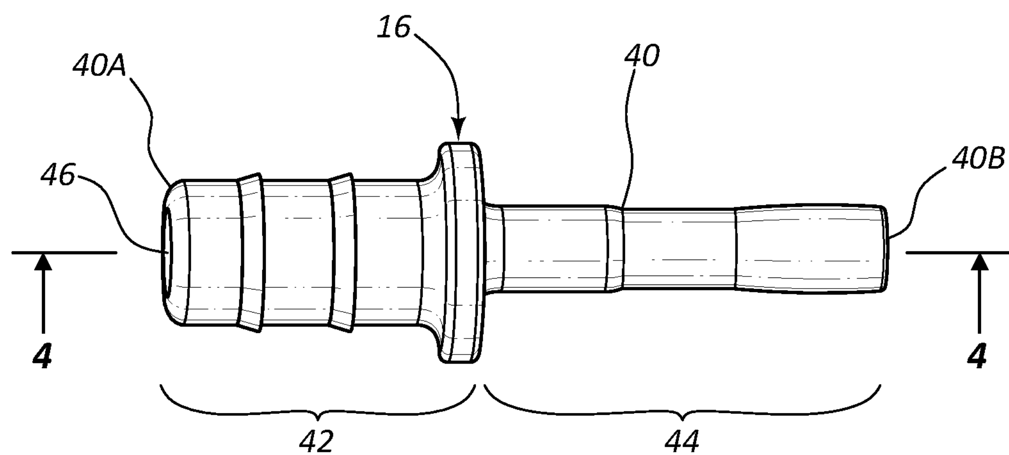
Figure 4:
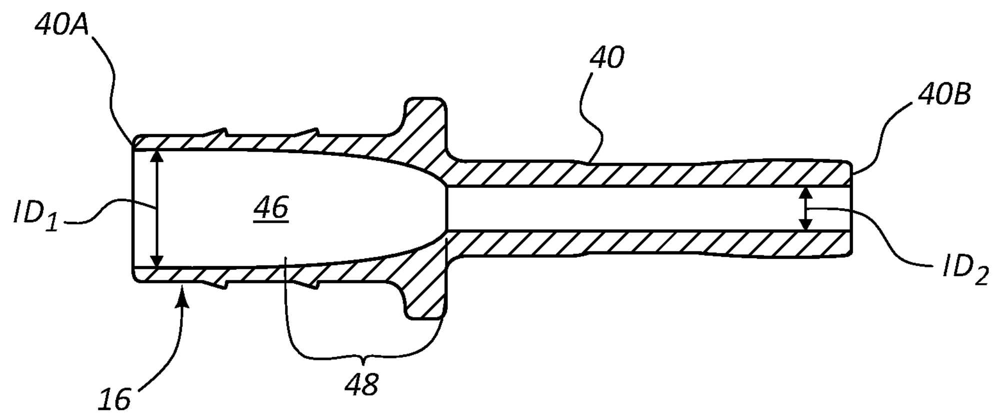
FIG. 4 is a cross-sectional view of the stem of FIGS. 3A and 3B.

FIGS. 3A-4 are various views of the stem 16 of the port 10 according to one embodiment. As shown, the stem 16 includes a body 40 extending between a proximal end 40A that is inserted into a hole defined in the body 12 of the port 10 and a distal end 40B that is configured to mate with a proximal end of a subcutaneously placed catheter. The stem body 40 defines a fluid conduit 46 that enables fluid to travel from the port reservoir 26 to a lumen of the catheter.

In greater detail, the fluid conduit 46 defines a proximal portion 42 extending distally from the proximal end 40A of the stem body 40 and a distal portion 44 extending proximally from the distal end 40B (FIG. 3B). In contrast with other stem designs, in the present embodiment the fluid conduit 46 defines a varying diameter configuration, wherein the proximal portion defines a relatively wide first inner diameter ID1 proximate the proximal end 40A of the stem body 40, as shown in FIG. 4. The first inner diameter ID1 reduces via a tapered transition region 48 to a second inner diameter ID2, which diameter extends through the distal portion 44 of the fluid conduit 46. The second inner diameter ID2 is sized in the present embodiment to enable fluid to be passed into the subcutaneous catheter attached over the distal end 40B of the stem 16 when the port 10 is disposed within the body of the patient.

The gradual transition in inner diameter from large (ID1) to relatively small (ID2) as described above in connection with FIG. 4 assists in reducing fluid pressure through the stem 16. This in turn improves flow characteristics and opens up options for port, stem, and catheter design. Note that, though here shown as having a gradual taper of a certain radius and length, the transition region 48 of the stem fluid conduit 46 can define other gradually changing cross-sectional shapes. Further, the relative sizes of the first and second inner diameters can vary from what is shown and described.

Figure 5:
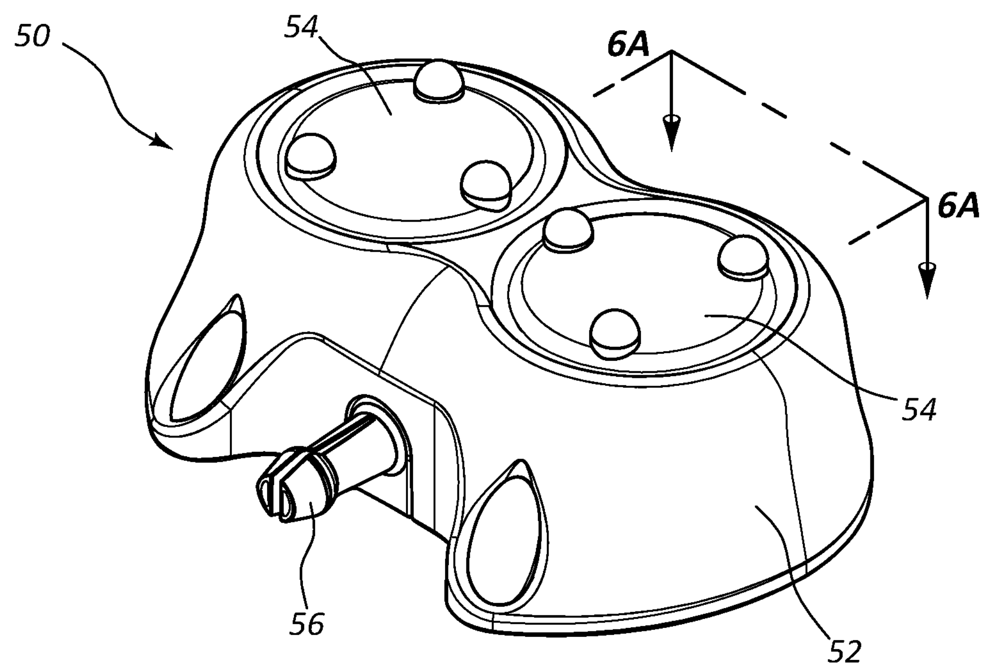
FIG. 5 is a perspective view of a dual-reservoir access port according to one embodiment.
Figure 6A:
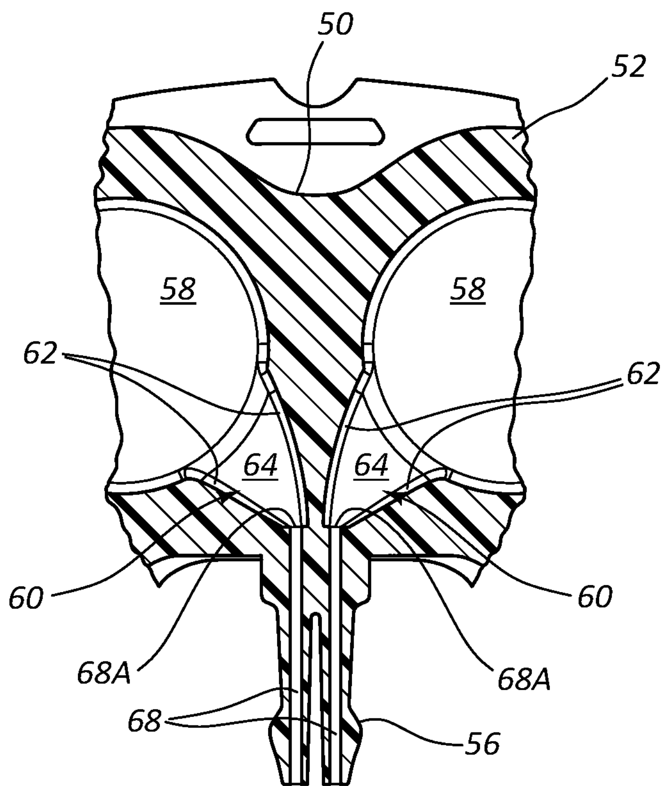
FIGS. 6A-6C are various cross-sectional views of the access port of FIG. 5.
Figure 6B:
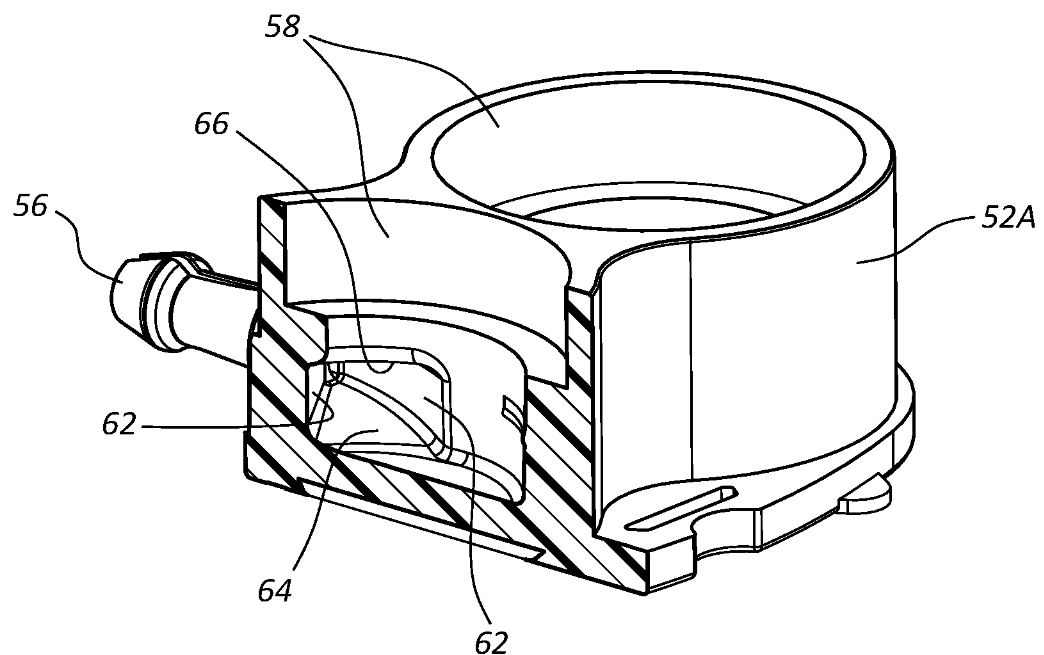
Figure 6C:
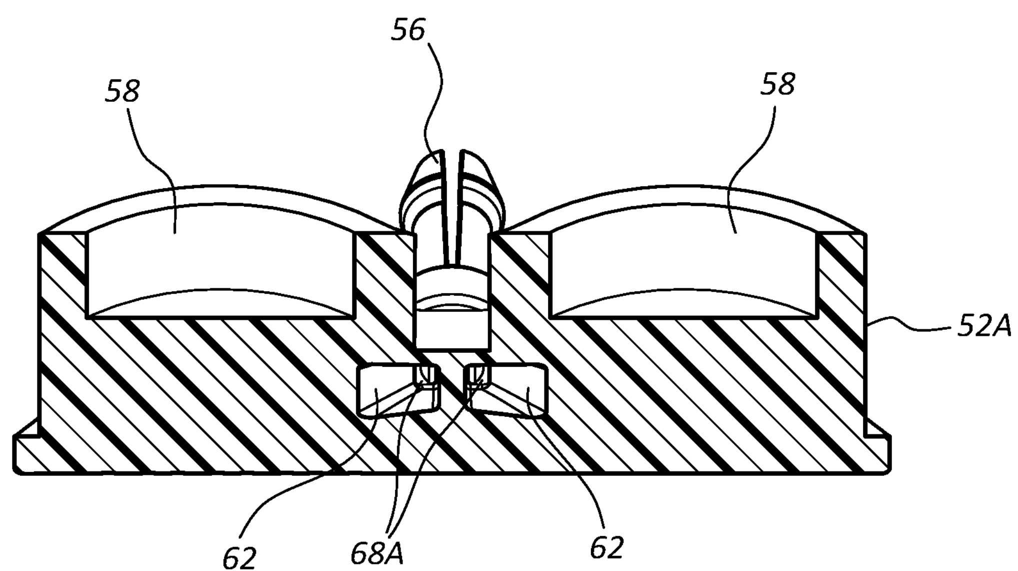

FIGS. 5-6C show details of a dual-reservoir port 50 according to one embodiment. The port 50 includes a body 52 and two septa 54 each attached so as to cover an aperture of a respective reservoir 58. A stem 56 including a fluid conduit 68 for each of the reservoirs 58 is also included.

As best seen in FIGS. 6A and 6B, a fluid outlet 60 is interposed between each of the reservoirs 58 and the corresponding fluid conduits 68 of the stem 56. In accordance with the present embodiment and in contrast with known designs, the fluid outlets 60 are tapered approaching each fluid conduit 68. In particular, each tapered fluid outlet 60 includes two side walls 62 that converge in a tapered fashion from the reservoir 58 toward a conduit entrance 68A of the respective stem fluid conduit 68. In addition, each fluid outlet 60 includes a floor 64 and a top wall 66, as best seen in the cross-sectional views of FIGS. 6B and 6C, which also converge in tapered fashion toward the respective conduit entrance 68A. In other embodiments it is appreciated that the floor, top wall, and side walls can have other positional relationships to one another, such as a tapering together of only the floor and top walls instead of the tapering of all walls, etc.

The above-described fluid pathway design assists in desirably reducing fluid pressures between the reservoirs 58 and the subcutaneous catheter connected to the distal end of the stem 56, compared to fluid outlet designs where the transition from the reservoir to the fluid conduit is relatively abrupt. Note that the particular degree of taper and size of the fluid outlets can be modified from what is shown and described herein while still residing within the principles of the present invention. Also, access ports of various configurations can benefit from the tapered fluid outlets described herein, including single-reservoir ports and ports with more than two reservoirs. In another embodiment, the tapered fluid outlets include a round cross section or other geometric shape.

Figure 7:
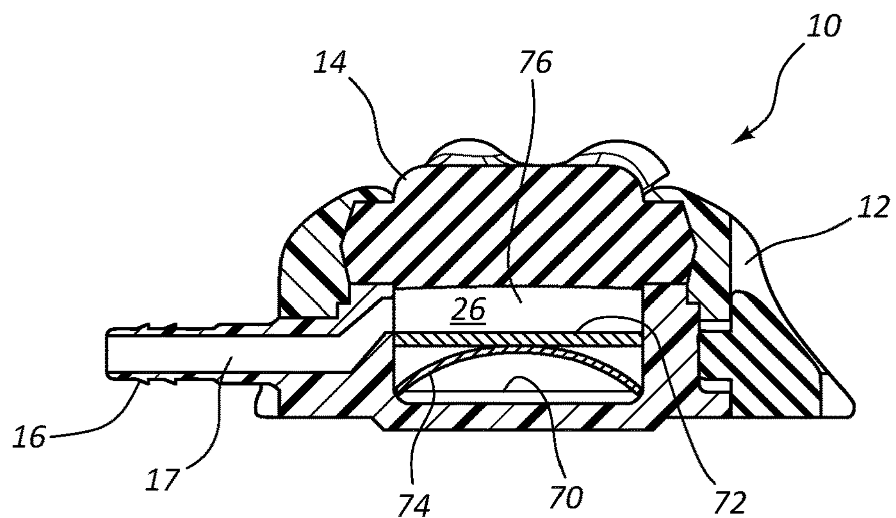
FIG. 7 is a cross sectional side view of an access port according to one embodiment.
Figure 8A:
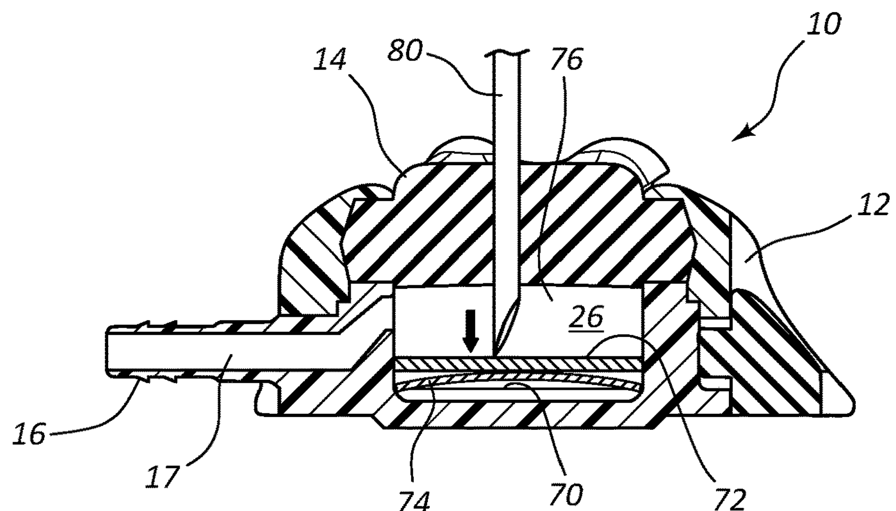
FIGS. 8A and 8B are various cross-sectional views of the access port of FIG. 7.
Figure 8B:
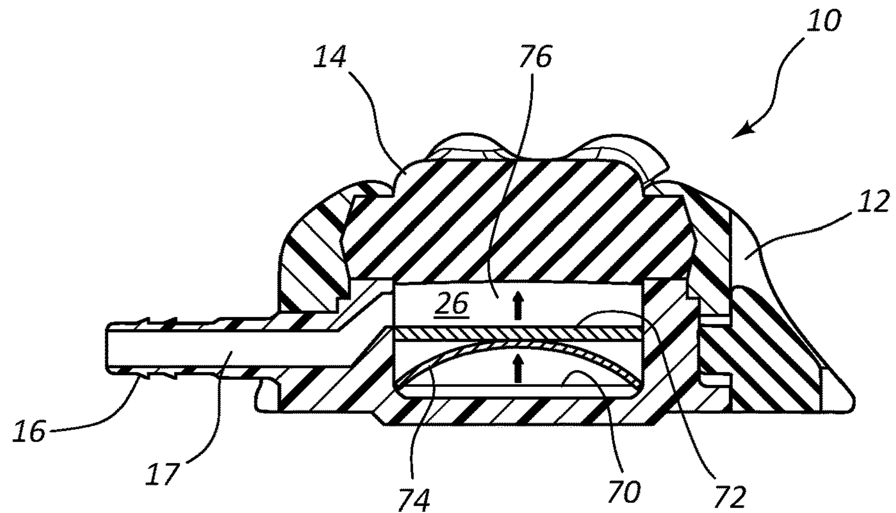

FIGS. 7-8B depict various details regarding an access port according to one embodiment, as shown, the port 10 includes a body 12 that captures a septum 14 that covers a reservoir 26. A stem 16 defining a fluid conduit 17 for the reservoir 26 is also included. As shown in FIG. 7, a movable floor 72 is disposed within the reservoir 26 in such a way as to be substantially parallel to a base 70 of the reservoir and to extend across the two-dimensional dimensions of the reservoir. For instance, in the case of the reservoir 26 including a round base 70, the floor 72 also defines a round two-dimensional shape. Of course, other reservoir and floor two-dimensional shapes are possible. The floor 72 can include a suitable material, such as metal, thermoplastic, etc.

A spring element 74 is interposed between the reservoir base 70 and the movable floor 72 to urge the floor into a height-extended first position, as seen in FIG. 7. The spring element 74 can include a spring washer, such as a Belleville washer or cupped spring washer, or other suitable element to provide a compliant urging force in the upward direction (from the perspective shown in FIG. 7) to maintain the floor in the first position of FIG. 7. In the first position, the floor 72 causes the reservoir 26 to define a first volume.

The spring element 74 is compressible to enable the floor 72 to be depressed into a reduced-height second position, shown in FIG. 8A. The floor 72 can be depressed by a needle 80 that is inserted through the septum 14 of the subcutaneously placed port 10. Such insertion of the needle 80 through the septum 14 and into contact with the floor 72 causes the floor to press on and compress the spring element 74 such that the floor moves into the reduced-height second position of FIG. 8A. With the floor 72 in this position, the reservoir 26 defines a second volume that is greater relative the first volume when the floor is in the first position. In this position, medicaments or other fluids can be injected through the reservoir 26 of the port 10 via the needle 80 for passage through the subcutaneous catheter attached to the stem 16. Similarly, fluids may be aspirated by the needle 80 from the catheter via the reservoir 26.

Once use of the port 10 is complete, the needle 80 can be removed from the septum 14. Removal of the needle 80 also removes the downward force provided thereby on the floor 72, which enables the spring element 74 to resiliently expand, causing the floor to rise from the reduced-height second position (FIG. 8A) back to the initial height-extended first position shown in FIG. 8B. This upward movement of the floor 72 reduces the volume of the reservoir 26 from the second volume (FIG. 8A) to the relatively smaller first volume (FIGS. 7, 8B). Such reduction of reservoir volume forces fluids still present in the reservoir 26 to escape out the conduit 17 of the stem 16 and through the catheter attached thereto, also referred to as a "positive flush." As a result, any blood or body fluid present in the catheter is flushed out of the catheter, thus preventing the undesired formation of blood clotting within the lumen of the catheter.

Note that other types of springs and resilient components can be employed for the spring element, and such components can vary in size, number, placement, etc. For instance, more than one Belleville washer can be disposed beneath the floor of the reservoir, in one embodiment. These and other variations are therefore contemplated.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An implantable access port, comprising:

a body defining a reservoir, the reservoir including:

a side wall including a side opening;

a top opening; and a bottom surface;

a volume control device positioned in the reservoir, the volume control device including:

a floor having an outer perimeter configured to provide a fluid seal against the side wall of the reservoir and a top surface parallel to the bottom surface of the reservoir, the floor designed to move from a height-extended first position below the side opening to a reduced-height second position adjacent the bottom surface; and a spring element positioned between the floor and the bottom surface, the spring element biasing the floor in the height-extended first position, wherein resilient expansion of the spring element moves the floor from the reduced-height second position to the height-extended first position to force fluids out of the reservoir;

a needle-penetrable septum covering the top opening of the reservoir, wherein a first volume of the reservoir is defined between a bottom of the needle-penetrable septum and the floor in the height-extended first position prior to insertion of a needle through the needle-penetrable septum; and a stem including a lumen in fluid communication with the side opening of the reservoir.

2. The implantable access port according to claim 1, wherein the spring element includes a spring washer.

3. The implantable access port according to claim 1, wherein the spring element includes a coil spring.

4. The implantable access port according to claim 1, wherein at least one of the body and the floor includes a thermoplastic.

5. The implantable access port according to claim 1, wherein the reservoir has a second volume greater than the first volume in the reduced-height second position of the floor.

6. The implantable access port according to claim 5, wherein movement of the floor from the reduced-height second position to the height-extended first position pushes fluid out of the reservoir through the side opening.

7. The implantable access port according to claim 6, wherein the stem is coupled to a catheter, and wherein movement of the floor from the reduced-height second position to the height-extended first position flushes a lumen of the catheter to prevent formation of clotting.

8. The implantable access port according to claim 1, further comprising a fluid outlet interposed between the side opening of the reservoir and the lumen of the stem.

9. The implantable access port according to claim 8, wherein the fluid outlet includes a top wall, a bottom wall, and opposing first and second sidewalls.

10. The implantable access port according to claim 9, wherein the top wall is substantially parallel to the bottom wall, and wherein the opposing first and second sidewalls taper toward one another.

11. The implantable access port according to claim 10, wherein the body includes a base portion and a cap portion, the fluid outlet defined in the base portion.

12. The implantable access port according to claim 1, wherein the lumen of the stem defines a proximal lumen portion of a first inner diameter, the proximal lumen portion positioned in the body, and a distal lumen portion of a second inner diameter smaller than the first inner diameter, the distal lumen portion extending outside of the body.

13. The implantable access port according to claim 12, wherein a tapered transition region is positioned between the proximal lumen portion and the distal lumen portion.

14. The implantable access port according to claim 1, wherein the stem includes a distal portion, the distal portion including a distal-most portion and a central portion, wherein an outer diameter of the distal-most portion is larger than an outer diameter of the central portion.

* * * * *